(12) United States Patent
Wunberg et al.

(10) Patent No.: US 8,314,113 B2
(45) Date of Patent: Nov. 20, 2012

(54) SUBSTITUTED DIHYDROQUINAZOLINES II

(75) Inventors: Tobias Wunberg, Hinterbruehl (AT); Judith Baumeister, Mechelen (BE); Mario Jeske, Solingen (DE); Peter Nell, Woodside, CA (US); Susanne Nikolic, Monheim (DE); Frank Suessmeier, Wuppertal (DE); Holger Zimmermann, Wuppertal (DE); Rolf Grosser, Leverkusen (DE); Guy Hewlett, Wuppertal (DE); Jorg Keldenich, Wuppertal (DE); Dieter Lang, Velbert (DE); Kerstin Henninger, Wuppertal (DE)

(73) Assignee: Aicuris GmbH & Co. KG, Wuppertal (DE)

( * ) Notice: Subject to any disclaimer, the term of this patent is extended or adjusted under 35 U.S.C. 154(b) by 1232 days.

(21) Appl. No.: 10/579,253

(22) PCT Filed: Oct. 28, 2004

(86) PCT No.: PCT/EP2004/012175
§ 371 (c)(1),
(2), (4) Date: Jun. 4, 2007

(87) PCT Pub. No.: WO2005/047278
PCT Pub. Date: May 26, 2005

(65) Prior Publication Data
US 2007/0281953 A1    Dec. 6, 2007

(30) Foreign Application Priority Data
Nov. 11, 2003 (DE) .................... 103 52 499

(51) Int. Cl.
*A01N 43/54* (2006.01)
*A61K 31/517* (2006.01)

(52) U.S. Cl. .................... 514/266.22; 544/284
(58) Field of Classification Search ............. 514/266.22; 544/283
See application file for complete search history.

(56) References Cited

U.S. PATENT DOCUMENTS

| | | | |
|---|---|---|---|
| 5,854,245 A | 12/1998 | Duggan et al. | |
| 7,196,086 B2 * | 3/2007 | Wunberg et al. | 514/252.17 |
| 7,271,260 B2 | 9/2007 | Lee et al. | |
| 7,709,491 B2 * | 5/2010 | Wunberg et al. | 514/266.1 |
| 7,960,387 B2 * | 6/2011 | Wunberg et al. | 514/252.17 |
| 2002/0019397 A1 | 2/2002 | Schnute et al. | |
| 2003/0216401 A1 | 11/2003 | Bentley et al. | |
| 2005/0065160 A1 | 3/2005 | Wunberg et al. | |
| 2006/0211683 A1 | 9/2006 | Selliah et al. | |
| 2006/0235032 A1 | 10/2006 | Wunberg et al. | |
| 2007/0066622 A1 | 3/2007 | Wunberg et al. | |
| 2007/0185121 A1 | 8/2007 | Wunberg et al. | |
| 2007/0281953 A1 | 12/2007 | Wunberg et al. | |
| 2008/0132515 A1 | 6/2008 | Wunberg et al. | |
| 2009/0221822 A1 * | 9/2009 | Goossen et al. | 544/292 |
| 2010/0179174 A1 | 7/2010 | Wunberg et al. | |
| 2010/0280021 A1 | 11/2010 | Berthel et al. | |

FOREIGN PATENT DOCUMENTS

| | | |
|---|---|---|
| EP | 1 201 765 | 5/2002 |
| WO | 9941253 | 8/1999 |
| WO | 2004041790 | 5/2004 |
| WO | 2004072048 | 8/2004 |
| WO | WO 2004072048 A1 * | 8/2004 |
| WO | WO-2004/096778 | 11/2004 |
| WO | WO-2004/099212 | 11/2004 |

OTHER PUBLICATIONS

Vippagunta et. al., "Crystalline solids", Advanced Drug Delivery Review, vol. 48 (2001), pp. 3-26.*
Stedman's Medical Dictionary 348 (William R. Henzyl et al., eds, 25th ed., 1990).*
B. Muller et al., Antiviral Strategies in, Antiviral Strategies 1-24, 4 (H.-G. Krausslich et al., eds., 2009).*
N.E. Sharpless et al., Nature Reviews Drug Discovery 1-14, 3 (2006).*
R.B. Freeman et al., 78 Transplantation 1765-1773 (Dec. 2004).*
D.J. Winston et al., 346 The Lancet 69-74 (1995).*
D. Mutimer, 25 Journal of Hepatology 259-269 (1996).*
D. Gold et al., 31 Antimicrobial Agents and Chemotherapy 361-367 (1987).*
R.J. Whitley et al., 26 Clinical Infectious Diseases, 541-553, 551 (1998).*
G. Hart et al., 11 Reviews in Medical Virology 73-81 (2001).*
G. M Cleator et al., The Herpesviridae in, Principles and Practice of Clinical Virology 23-26, 23 (Arie J. Zuckerman et al., eds., 5th ed., 2004).*
P.E. Pellett et al., The Family Herpesviridae: A Brief Introduction in, Fields' VIROLOGY 2479-2499, 2480 (David M. Knipe et al., eds., 5th ed., 2007).*
J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
P.D. Griffiths, Cytomegalovirus in, Principles and Practice of Clinical Virology 85-122 (A.J. Zuckerman et al., eds, 5th ed., 2001).*
G. M Cleator et al., Herpes Simplex in, Principles and Practice of Clinical Virology 27-51, 44 (Arie J. Zuckerman et al., eds., 5th ed., 2004).*
D.M. Nowlin et al., 65 Journal of Virology 3114-3121 (1991).*
N.J. Schmidt et al., 4 Journal of Clinical Microbiology, 61-66, 62 (1976).*
R.C. Condit, Principals of Virology in, Fields' Virology 25-57, 37-38 (David M. Knipe et al., eds., 5th ed., 2007).*
N.E. Sharpless et al., Nature Reviews Drug Discovery 1-14, 2 (2006).*
B. Hann et al., Current Opinion in Cell Biology, 13, 778-784 (2001).*
B. Muller et al., Antiviral Strategies in, Antiviral Strategies 1-24, 7 (H.-G. Krausslich et al., eds., 2009).*

(Continued)

*Primary Examiner* — James O Wilson
*Assistant Examiner* — Alexander R Pagano
(74) *Attorney, Agent, or Firm* — Morrison & Foerster LLP

(57) ABSTRACT

The invention relates to substituted dihydroquinazolines and to a method for the production thereof, the use thereof for treating and/or preventing diseases and for producing drugs for treating and/or preventing diseases, in particular for the use of the inventive dihydroquinazolines in the form of antiviral agents, in particular against cytomegaloviruses.

10 Claims, No Drawings

OTHER PUBLICATIONS

Martinez et al., Antiviral Chem. Chemo. (2003) 14:107-114.
Gribaudo et al., Virus Research (2001) 73:57-65.
Takao Saito, et al., "A Facile and Efficient Carbodiimide-Mediated Synthesis of Dihydroquinazolines via a Tandem Nucleophilic Addition-Intramolecular Hetero Conjugate Addition Annulation Strategy", Tetrahedron Letters, 1996, vol. 37 No. 2, pp. 209-212.
Fengjiang Wang, el al., "Solid-Phase Synthesis of 3,4-Dihydroquinazoline", Tetrahedron Letters, 1997, vol. 38 No. 50, pp. 8651-8654.
Yong Sup Lee, et al., "3,4-Dihydroquinazoline Derivatives as Novel Selective T-type Ca2+ Channel Blockers", Bioorganic & Medicinal Chemistry Letters, 2004, vol. 14, pp. 3379-3384.
Desai et al., Indian J. Exp. Biol. (1998) 36(12):1280-1283 (abstract).
Desai et al., Farmaco (1996) 51(5):361-366 (abstract).
Griesser, Chapter 8, The Importance of Solvates (pp. 211-230), in the text, Polymorphism: In the Pharmaceutical Industry, Hilfiker, 2006.
Lischka et al., Current Opinion in Pharmacology (Article in Press, Corrected Proof) (2008) 8:1-8.
Molina et al., Synthesis (1998) 3:283-287.
Search Report from Ecuadorian Patent Application No. SP 05-6138, received Dec. 20, 2010, 1 page.
Vippagunta et al., Advanced Drug Delivery Review (2001) 48:3-26.
Viral Defense Found., http://www.viraldefense.org/mission.htm, downloaded Oct. 21, 2008.
Visiting Nurse Assns. of America, http://www.vnaa.org/vnaa/gen/Germ_Protection_Center_Cold_and_Flu_Resources, downloaded Oct. 21, 2008.
Wikipedia, Maribavir, updated Feb. 10, 2009, http://en.wikipedia.org/wiki/Maribavir, downloaded Mar. 10, 2009.
Wilson et al., Med. Chem. Res. (1992) 2:102-110 (abstract).
Xin et al., Tetrahedron Lett. (2000) 41(8):1147-1150.
Zimmermann et al., "Letermovir (AIC246)—A Novel Drug Under Development for Prevention and Treatment of Cytomegalovirus Infections Acting via a Novel Mechanism of Action", European Infectious Disease (2011) 5(2):112-114.

* cited by examiner

SUBSTITUTED DIHYDROQUINAZOLINES II

The invention relates to substituted dihydroquinazolines and to processes for their preparation, to their use for the treatment and/or prophylaxis of diseases and to their use for preparing medicaments for the treatment and/or prophylaxis of diseases, in particular for use as antiviral agents, especially against cytomegaloviruses.

The synthesis of dihydroquinazolines is described in Saito T. et al., Tetrahedron Lett., 1996, 37, 209-212, and in Wang F. et al., Tetrahedron Lett., 1997, 38, 8651-8654. Furthermore, Y. S. Lee et al., *Bioorg. Med. Chem. Lett.*, 2004, 14, 3379-3384, have described dihydroquinazolines as calcium channel inhibitors.

Agents with antiviral activity and a different structure are available on the market; however, the therapies currently available with ganciclovir, valganciclovir, foscarnet and cidofovir are associated with severe side effects, for example nephrotoxicity, neutropenia or thrombocytopenia. In addition, it is always possible for resistance to develop. Novel agents for an effective therapy are therefore desirable.

One object of the present invention is therefore to provide novel compounds having the same or improved antiviral action for the treatment of viral infective diseases in humans and animals.

It has been found, surprisingly, that the substituted dihydroquinazolines described in the present invention have high antiviral activity.

The invention provides compounds of the formula

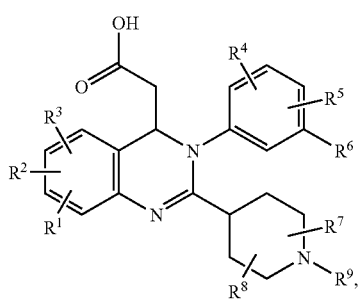

in which $R^1$, $R^2$ and $R^3$ independently of one another represent hydrogen, alkyl, alkoxy, carboxyl, alkylcarbonyl, alkoxycarbonyl, aminocarbonyl, trifluoromethyl, halogen, cyano, hydroxyl or nitro, $R^4$ and $R^5$ independently of one another represent hydrogen, alkyl, alkoxy, alkylthio, cyano, halogen, nitro, trifluoromethyl or trifluoromethoxy, $R^6$ represents alkyl, cyano, halogen, nitro or trifluoromethyl, $R^7$ and $R^8$ independently of one another represent hydrogen, halogen, alkyl or alkoxy and $R^9$ represents aryl or 1,3-benzodioxol-5-yl, where aryl and 1,3-benzodioxol-5-yl may be substituted by 1 to 3 substituents, where the substituents independently of one another are selected from the group consisting of alkoxy, alkylthio, carboxyl, alkylcarbonyl, alkoxycarbonyl, aminocarbonyl, trifluoromethyl, halogen, carbamoyl, cyano, hydroxyl, amino, alkylamino, nitro and optionally hydroxyl-substituted alkyl, and their salts, their solvates and the solvates of their salts.

Compounds according to the invention are the compounds of the formula (I) and their salts, solvates and solvates of the salts, compounds mentioned hereinbelow as exemplary embodiment(s) and their salts, solvates and solvates of the salts, if the compounds mentioned hereinbelow, embraced by formula (I), are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can exist in tautomeric forms, the present invention provides all tautomeric forms.

Salts in the context of the present invention are preferably physiologically acceptable salts of the compounds according to the invention. Also provided, however, are salts which for their part are not suitable for pharmaceutical applications but which can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates are those forms of the compounds according to the invention which form a complex in the solid or liquid state by coordination with solvent molecules. Hydrates are a special form of solvates in which the coordination takes place with water.

For the purposes of the present invention, unless specified otherwise, the substituents have the following meanings:

Alkyl per se and "alk" and "alkyl" in alkoxy, alkylthio, alkylamino, alkylcarbonyl and alkoxycarbonyl represent a straight-chain or branched alkyl radical having generally 1 to 6 ("$C_1$-$C_6$-alkyl"), preferably 1 to 4, particularly preferably 1 to 3, carbon atoms, by way of example and preferably methyl, ethyl, n-propyl, isopropyl, tert-butyl, n-pentyl and n-hexyl.

Alkoxy represents, by way of example and preferably, methoxy, ethoxy, n-propoxy, isopropoxy, tert-butoxy, n-pentoxy and n-hexoxy.

Alkylthio represents, by way of example and preferably, methylthio, ethylthio, n-propylthio, isopropylthio, tert-butylthio, n-pentylthio and n-hexylthio.

Alkylcarbonyl represents, by way of example and preferably, acetyl and propanoyl.

Alkylamino represents an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-Alkylamino is, for example, a monoalkylamino radical having 1 to 3 carbon atoms or is a dialkylamino radical having 1 to 3 carbon atoms each per alkyl substituent.

Alkoxycarbonyl represents, by way of example and preferably, methoxycarbonyl, ethoxycarbonyl, n-propoxycarbonyl, isopropoxycarbonyl, tert-butoxycarbonyl, n-pentoxycarbonyl and n-hexoxycarbonyl.

Aryl represents a mono- to tricyclic aromatic carbocyclic radical having generally 6 to 14 carbon atoms; by way of example and preferably phenyl, naphthyl and phenanthrenyl.

Halogen represents fluorine, chlorine, bromine and iodine.

A symbol * on a carbon atom means that the compound, with respect to the configuration at this carbon atom, is present in enantiomerically pure form which, for the purposes of the present invention, is to be understood as meaning an enantiomeric excess of more than 90% (>90% ee).

In the context of the present invention, preference is given to compounds of the formula (I)
in which
$R^1$, $R^2$ and $R^3$ independently of one another represent hydrogen, fluorine, chlorine, cyano, hydroxyl or aminocarbonyl,
$R^4$ and $R^5$ independently of one another represent hydrogen, fluorine, alkyl or alkoxy,
$R^6$ represents chlorine, nitro, trifluoromethyl, methyl, isopropyl or tert-butyl,
$R^7$ and $R^8$ independently of one another represent hydrogen or $C_1$-$C_3$-alkyl and
$R^9$ represents phenyl or 1,3-benzodioxol-5-yl, where phenyl may be substituted by 1 to 3 substituents, where the substituents independently of one another are selected from the group consisting of $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino and nitro,
and their salts, their solvates and the solvates of their salts.

In the context of the present invention, preference is given to compounds of the formula (I)
in which
$R^1$, $R^2$ and $R^3$ independently of one another represent hydrogen, methyl, fluorine, chlorine, cyano, hydroxyl or aminocarbonyl,
$R^4$ and $R^5$ independently of one another represent hydrogen, fluorine, $C_1$-$C_4$-alkyl or $C_1$-$C_4$-alkoxy,
$R^6$ represents chlorine, nitro, trifluoromethyl, methyl, isopropyl or tert-butyl,
$R^7$ and $R^8$ independently of one another represent hydrogen or $C_1$-$C_3$-alkyl and
$R^9$ represents phenyl or 1,3-benzodioxol-5-yl, where phenyl may be substituted by 1 to 3 substituents, where the substituents independently of one another are selected from the group consisting of $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino and nitro,
and their salts, their solvates and the solvates of their salts.

In the context of the present invention, preference is also given to compounds of the formula (I)
in which
$R^1$ and $R^2$ represent hydrogen,
$R^3$ represents fluorine,
$R^4$ and $R^5$ independently of one another represent hydrogen, fluorine or alkoxy,
$R^6$ represents trifluoromethyl,
$R^7$ and $R^8$ represent hydrogen, and
$R^9$ represents phenyl, where phenyl may be substituted by 1 or 2 substituents, where the substituents independently of one another are selected from the group consisting of methyl, methoxy, fluorine and chlorine,
and their salts, their solvates and the solvates of their salts.

In the context of the present invention, preference is also given to con pounds of the formula (I)
in which
$R^1$ and $R^2$ are hydrogen,
$R^3$ is fluorine,
$R^4$ and $R^5$ independently of one another are hydrogen, fluorine or methoxy,
$R^6$ is trifluoromethyl,
$R^7$ and $R^8$ are hydrogen and
$R^9$ is phenyl, where phenyl may be substituted by 1 or 2 substituents, where the substituents independently of one another are selected from the group consisting of methyl, methoxy, ethoxy, fluorine and chlorine,
and their salts, their solvates and the solvates of their salts.

In the context of the present invention, preference is also given to compounds of the formula (I) in which $R^1$ and $R^2$ represent hydrogen.

In the context of the present invention, preference is also given to compounds of the formula (I) in which $R^3$ is attached to the carbon atom in position 6 or position 8 of the quinazoline skeleton.

In the context of the present invention, preference is also given to compounds of the formula (I) in which $R^3$ is attached to the carbon atom in position 8 of the quinazoline skeleton.

In the context of the present invention, preference is also given to compounds of the formula (I) in which $R^3$ represents fluorine, in particular fluorine which is attached to the carbon atom in position 8 of the quinazoline skeleton.

In the context of the present invention, preference is also given to compounds of the formula (I) in which $R^4$ and $R^5$ represent hydrogen.

In the context of the present invention, preference is also given to compounds of the formula (I) in which $R^4$ represents hydrogen and $R^5$ represents fluorine or alkoxy.

In the context of the present invention, preference is also given to compounds of the formula (I) in which $R^4$ represents hydrogen and $R^5$ represents methoxy.

In the context of the present invention, preference is also given to compounds of the formula (I) in which $R^6$ represents trifluoromethyl.

In the context of the present invention, preference is also given to compounds of the formula (I) in which $R^6$ represents methyl, isopropyl or tert-butyl.

In the context of the present invention, preference is also given to compounds of the formula (I) in which $R^6$ represents isopropyl or tert-butyl.

In the context of the present invention, preference is also given to compounds of the formula (I) in which $R^7$ and $R^8$ represent hydrogen.

In the context of the present invention, preference is also given to compounds of the formula (I) in which $R^9$ represents phenyl, where phenyl may be substituted by 1 or 2 substituents, where the substituents independently of one another are selected from the group consisting of methyl, methoxy, fluorine and chlorine.

In the context of the present invention, preference is also given to compounds of the formula (I) in which $R^9$ represents phenyl, where phenyl is substituted by fluorine in the para-position to the point of attachment to the piperidine ring.

In the context of the present invention, preference is also given to compounds of the formula (I) in which $R^9$ represents phenyl, where phenyl is substituted by chlorine, methyl or methoxy in the meta-position to the point of attachment to the piperidine ring.

In the context of the present invention, preference is also given to compounds of the formula (I) in which $R^9$ represents phenyl, where phenyl is substituted by methyl in the meta-position to the point of attachment to the piperidine ring and by fluorine in the para-position to the point of attachment to the piperidine ring.

The invention furthermore provides a process for preparing the compounds of the formula (I), where compounds of the formula

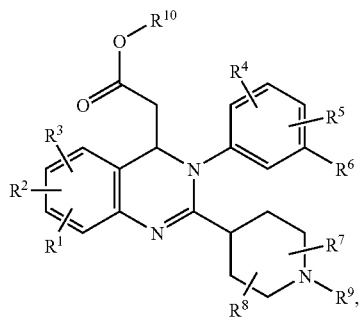

(II)

in which
$R^1, R^2, R^3, R^4, R^5, R^6, R^7, R^8$ and $R^9$ are as defined above, and $R^{10}$ represents alkyl, preferably methyl or ethyl,
are reacted with bases.

The reaction is generally carried out in inert solvents, preferably in a temperature range of from room temperature to the reflux of the solvents at atmospheric pressure.

Bases are, for example, alkali metal hydroxides, such as sodium hydroxide, lithium hydroxide or potassium hydroxide, or alkali metal carbonates, such as caesium carbonate, sodium carbonate or potassium carbonate, if appropriate in aqueous solution; preference is given to sodium hydroxide in water.

Inert solvents are, for example, halogenated hydrocarbons, such as ethers, such as 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, or of mixtures of solvents; preference is given to dioxane or tetrahydrofuran.

The compounds of the formula (II) are known or can be prepared by reacting compounds of the formula

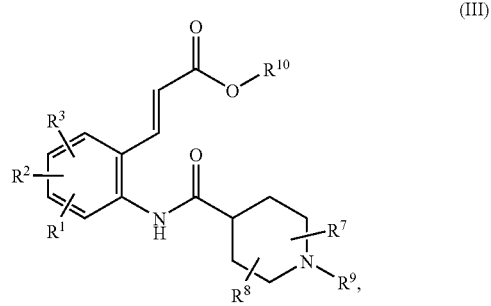

(III)

in which
$R^1, R^2, R^3, R^7, R^8, R^9$ and $R^{10}$ are as defined above, with compounds of the formula

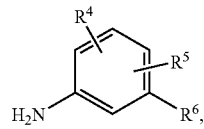

(IV)

in which
$R^4, R^5$ and $R^6$ are as defined above,
in the presence of phosphorus oxychloride.

The reaction is generally carried out in inert solvents, preferably in a temperature range of from 50° C. to the reflux of the solvents at atmospheric pressure.

Inert solvents are, for example, hydrocarbons, such as benzene, xylene, toluene, hexane, cyclohexane or mineral oil fractions; preference is given to toluene.

Alternatively, the compounds of the formula (II) can be prepared in a two-step synthesis process. In the first step, the compounds of the formula (III) are heated with phosphorus oxychloride in an inert solvent, preferably toluene, under reflux at atmospheric pressure. The solvent is removed. In the second step, the compounds obtained in this manner are reacted with compounds of the formula (IV) in an inert solvent, preferably toluene, likewise under reflux at atmospheric pressure.

The compounds of the formula (IV) are known or can be synthesized by known processes from the appropriate starting materials.

The compounds of the formula (III) are known or can be prepared by reacting compounds of the formula

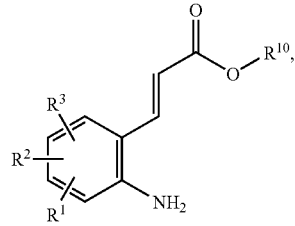

(V)

in which $R^1$, $R^2$, $R^3$ and $R^{10}$ are as defined above, with compounds of the formula

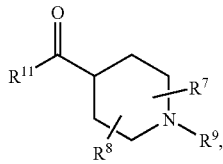

(VI)

in which $R^7$, $R^8$ and $R^9$ are as defined above, and $R^{11}$ represents halogen, preferably chlorine, bromine or iodine, or hydroxyl.

In the case that $R^{11}$ represents hydroxyl, the reaction is generally carried out in inert solvents, in the presence of customary condensing agents, if appropriate in the presence of a base, preferably in a temperature range of from room temperature to 50° C. at atmospheric pressure.

Inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, dioxane, tetrahydrofuran, 1,2-dimethoxyethane, glycol dimethyl ether or diethylene glycol dimethyl ether, hydrocarbons, such as benzene, xylene, toluene, hexane, cyclohexane or mineral oil fractions, or carboxamides, such as dimethylformamide or dimethylacetamide, alkylnitriles, such as acetonitrile, or heteroaromatic compounds, such as pyridine, or ethyl acetate; preference is given to tetrahydrofuran, 1,2-dichloroethane or methylene chloride.

Customary condensing agents are, for example, carbodiimides, such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds, such as carbonyldiimidazole, or 1,2-oxazolium compounds, such as 2-ethyl-5-phenyl-1,2-oxazolium 3-sulphate, or 2-tert-butyl-5-methyl-isoxazolium perchlorate, or acylamino compounds, such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzo-triazolyloxytri(dimethylamino) phosphonium hexafluorophosphate, or O-(benzo-triazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPIU) or O-(7-azabenzotriazol-1-yl)-N,N,N',N'-tetramethyluronium hexafluorophosphate (HATU), or 1-hydroxybenzotriazole (HOBt), or benzotriazol-1-yloxy-tris(dimethylamino)phosphonium hexafluorophosphate (BOP), or mixtures of these.

Bases are, for example, alkali metal carbonates, such as, for example, sodium carbonate or potassium carbonate, or sodium bicarbonate or potassium bicarbonate, or organic bases, such as trialkylamines, for example triethylamine, N-methyl-morpholine, N-methylpiperidine, 4-dimethylaminopyridine or diisopropylethylamine.

Particular preference is given to the combination of N-(3-dimethylaminoisopropyl)-N'-ethylcarbodiimide hydrochloride (EDC), 1-hydroxybenzotriazole (HOBt) and triethylamine and dimethylformamide or carbonyldiimidazole in 1,2-dichloroethane.

In the case that $R^{11}$ represents halogen, the reaction is generally carried out in inert solvents, if appropriate in the presence of a base, preferably in a temperature range of from 0° C. to 50° C. at atmospheric pressure.

Inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, dioxane, tetrahydrofuran, 1,2-dimethoxyethane, glycol dimethyl ether or diethylene glycol dimethyl ether, hydrocarbons, such as benzene, xylene, toluene, hexane, cyclohexane or mineral oil fractions, or carboxamides, such as dimethylformamide or dimethylacetamide, alkylnitriles, such as acetonitrile, or heteroaromatic compounds, such as pyridine, or ethyl acetate; preference is given to tetrahydrofuran, dioxane or methylene chloride.

Bases are, for example, alkali metal carbonates, such as caesium carbonate, sodium carbonate or potassium carbonate, alkali metal acetates, such as sodium acetate, or other bases, such as triethylamine or diisopropylethylamine, preferably diisopropylethylamine or triethylamine.

The compounds of the formula (VI) are known or can be synthesized by known processes from the appropriate starting materials.

The compounds of the formula (V) are known or can be prepared by known processes from the appropriate starting materials, for example by a Heck reaction or a Wittig-Horner reaction according to the synthesis schemes below:

Heck Reaction:

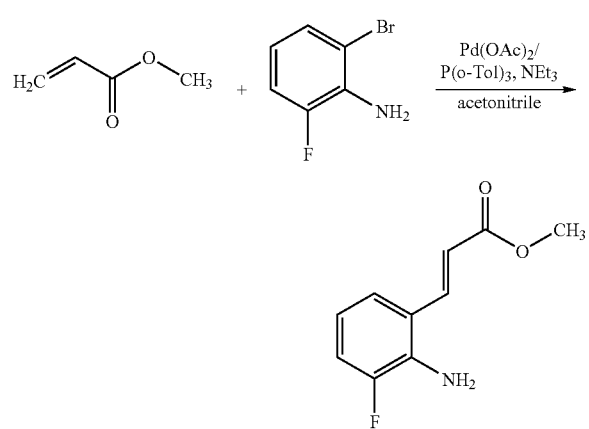

Wittig-Horner Reaction:

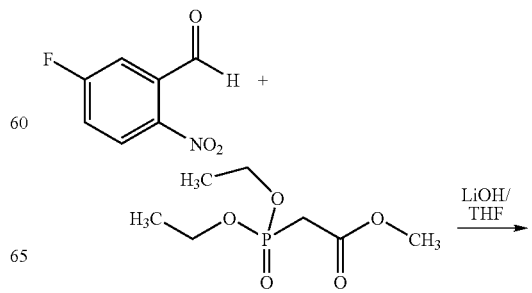

-continued
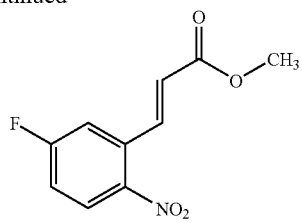
The starting materials required for this purpose are known or can be synthesized by known processes from the appropriate starting materials.
The preparation of the compounds according to the invention can be illustrated by the synthesis scheme below.
Synthesis Scheme:
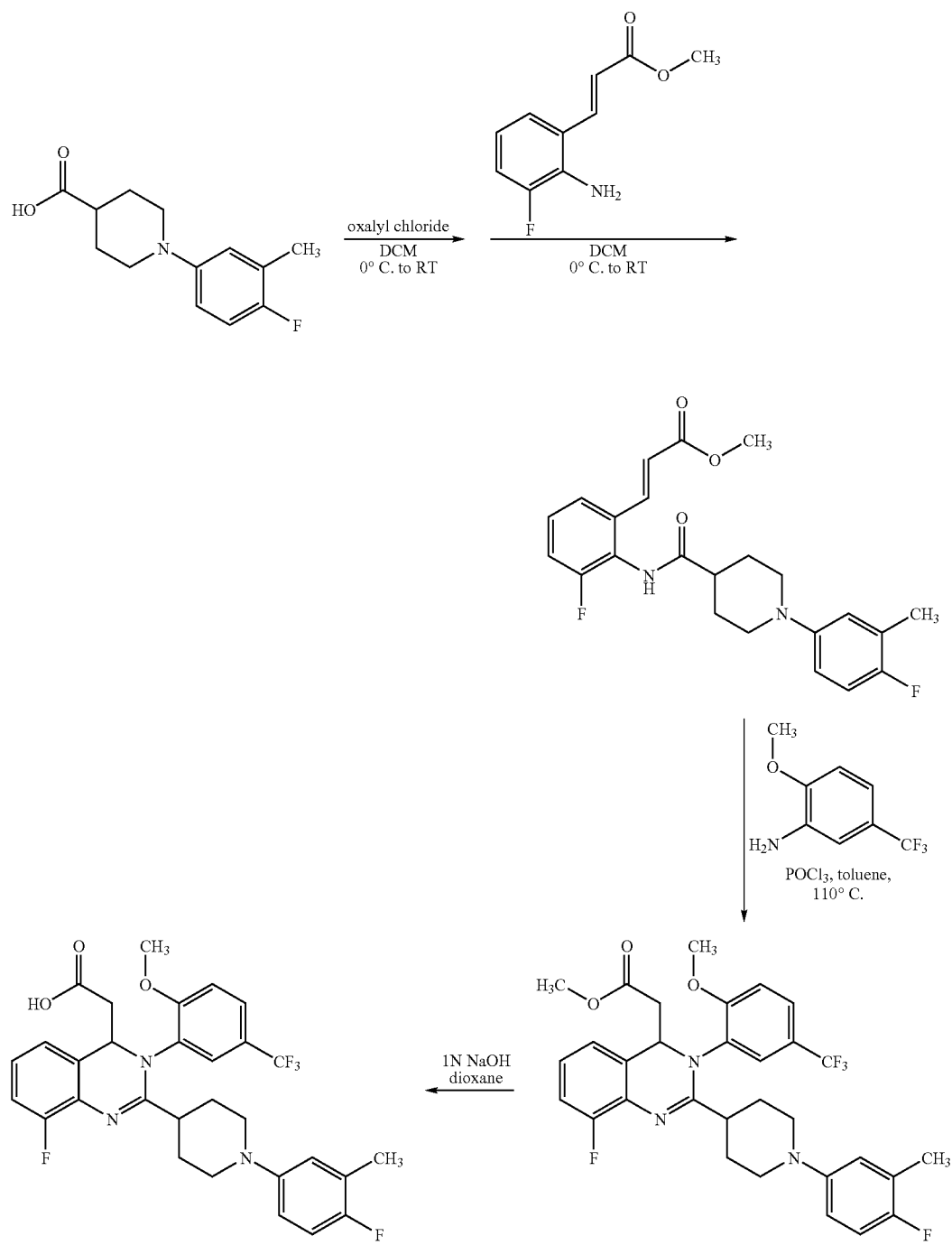

The compounds of the general formula (I) according to the invention show a surprising range of effects which could not have been predicted. They show an antiviral effect on representatives of the group of the Herpes viridae (Herpes viruses), especially on cytomegaloviruses (CMV), in particular on the human cytomegalovirus (HCMV).

Areas of indication which may be mentioned by way of example are:
1) Treatment and prophylaxis of HCMV infections in AIDS patients (retinitis, pneumonitis, gastrointestinal infections).
2) Treatment and prophylaxis of cytomegalovirus infections in bone-marrow and organ transplantation patients who develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of HCMV infection in immunosuppressed patients associated with cancer and cancer therapy.
6) Treatment of HCMV-positive cancer patients with the target to reduce HCMV-mediated tumour progression (cf. J. Cinatl et al., *FEMS Microbiology Reviews* 2004, 28, 59-77).

The present invention furthermore provides the use of the compounds according to the invention for the treatment and/or prophylaxis of diseases, especially viral infections, in particular with the viruses mentioned above, and the infective diseases caused thereby. Hereinbelow, a viral infection is to be understood as meaning both an infection with a virus and a disease caused by an infection with a virus.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The compounds according to the invention are preferably used for preparing medicaments suitable for the prophylaxis and/or treatment of infections with a representative of the group of the Herpes viridae, in particular a cytomegalovirus, in particular the human cytomegalovirus.

The present invention furthermore provides a method for the treatment and/or prophylaxis of disorders, in particular the disorders mentioned above, using an anti-virally effective amount of the compounds according to the invention.

The present invention furthermore provides medicaments comprising at least one compound according to the invention and at least one or more further, active compounds, in particular for the treatment and/or prophylaxis of the disorders mentioned above. Active compounds which may be mentioned by way of example and by way of preference as being suitable for combinations are: antiviral active compounds, such as gancyclovir or acyclovir.

The compounds according to the invention can act systemically and/or locally. For this purpose, they can be administered in a suitable way, such as, for example, by the oral, parenteral, pulmonary, nasal, sublingual, lingual, buccal, rectal, dermal, transdermal, conjunctival or otic route, or as implant or stent.

For these administration routes, it is possible to administer the compounds according to the invention in suitable administration forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (uncoated and coated tablets, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitonealy). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems, milk, pastes, foams, dusting powders, implants or stents.

The active compounds according to the invention can be converted into the stated administration forms. This can take place in a manner known per se by mixing with inert nontoxic, pharmaceutically acceptable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert non-toxic, pharmaceutically acceptable auxiliaries, and their use for the purposes mentioned above.

In general, it has proved advantageous to administer on intravenous administration amounts of from about 0.001 to 10 mg/kg, preferably from about 0.01 to 5 mg/kg, of body weight to achieve effective results, and the dosage on oral administration is from about 0.01 to 25 mg/kg, preferably from 0.1 to 10 mg/kg, of body weight.

It may nevertheless be necessary, where appropriate, to deviate from the amounts mentioned, depending on the body weight, the administration route, the individual response to the active compound, the mode of preparation and the time or interval over which administration takes place. Thus, in some cases it may be sufficient to make do with less than the aforementioned minimal amount, whereas in other cases the upper limit mentioned must be exceeded. In the event of administration of larger amounts, it may be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

Abbreviations Used:

| | |
|---|---|
| BINAP | 2,2'-bis(diphenylphosphino)-1,1'-binaphthyl |
| CDCl$_3$ | deuterochloroform |
| CD$_3$CN | deuteroacetonitrile |
| TLC | thin-layer chromatography |
| DCI | direct chemical ionization (in MS) |
| DCM | dichloromethane |
| DIEA | N,N-diisopropylethylamine (Hünig base) |
| DMSO | dimethyl sulphoxide |
| DMF | N,N-dimethylformamide |
| EA | ethyl acetate |
| EI | electron impact ionization (in MS) |
| ESI | electrospray ionization (in MS) |
| m.p. | melting point |
| sat. | saturated |
| h | hour |
| HPLC | high-pressure, high-performance liquid chromatography |
| conc. | concentrated |
| LC-MS | liquid chromatography-coupled mass spectroscopy |
| LDA | lithium diisopropylamide |
| MS | mass spectroscopy |
| NMR | nuclear magnetic resonance spectroscopy |
| RP-HPLC | reverse phase HPLC |
| RT | room temperature |
| R$_t$ | retention time (in HPLC) |
| THF | tetrahydrofuran |

General LCMS and HPLC Methods:

Method 1 (HPLC): Instrument: HP 1100 with DAD detection; column: Kromasil RP-18, 60 mm×2 mm, 3.5 µm; mobile phase A: 5 ml of HClO$_4$/l of water, mobile phase B: acetonitrile; gradient: 0.0 min 2% B, 0.5 min 2% B, 4.5 min 90% B, 6.5 min 90% B; flow rate: 0.75 ml/min; oven: 30° C.; UV detection: 210 nm.

Method 2 (HPLC, separation of enantiomers): chiral silica gel selector KBD 6136 (10 µm, 350×30 mm) based on the selector poly(N-methacryloyl-L-leucine-1-methylamide); temperature: 24° C.; flow rate: 50 ml/min; UV detection: 254 nm; sample application in ethyl acetate; elution mixtures of isohexane (A)/ethyl acetate (B), for example: gradient: →0.0 min 40% B→9.0 min 40% B→9.01 min 100% B→12.0 min 100% B→12.01 min 40% B→15 min 40% B.

Method 3 (LCMS): MS instrument type: Micromass ZQ; HPLC instrument type: HP 1100 Series; UV DAD; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (HPLC, preparative separation): column: Crom-Sil C18, 250 mm×30 mm; mobile phase A: water, mobile phase B: acetonitrile; gradient: 3 min 10% B→31 min 90% B→34 min 90% B→34.01 min 10% B; run time: 38 min; flow rate: 50 ml/min; UV detection: 210 nm.

Method 5 (LCMS): MS instrument type: Micromass ZQ; HPLC instrument type: Waters Alliance 2795; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 6 (HPLC): instrument: HP 1100 with DAD detection; column: Kromasil RP-18, 60 mm×2 mm, 3.5 µm; mobile phase A: 5 ml of HClO$_4$/l of water, mobile phase B: acetonitrile; gradient: 0.0 min 2% B, 0.5 min 2% B, 4.5 min 90% B, 9 min 90% B; flow rate: 0.75 ml/min; oven: 30° C.; UV detection: 210 nm.

Method 7 (LC-MS): instrument: Micromass Platform LCZ with HPLC Agilent Series 1100; column: Grom-SIL120 ODS-4 HE, 50 mm×2.0 mm, 3 µm; mobile phase A: 1 l of water+1 ml of 50% strength formic acid, mobile phase B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 210 nm.

Working Examples

General Procedure [A]: Synthesis of Substituted 2-aminocinnamic Acid Derivatives from 2-halo-substituted Anilines by Heck Coupling In a one-necked flask, 1.0 equivalent of an aryl halide is initially charged in acetonitrile with 1.6 equivalents of methyl acrylate, 2.0 equivalents of triethylamine, 0.03 equivalents of palladium(II) acetate and 0.03 equivalents of tri-o-tolylphosphine (about 1M solution). The mixture is stirred under reflux for 48 hours. After the reaction has ended (the reaction is monitored by TLC), the solvent is removed. The residue is purified chromatographically on silica gel using cyclohexane/ethyl acetate=8:2 v/v.

Example 1A

Methyl (2E)-3-[2-amino-3-fluorophenyl]propenoate

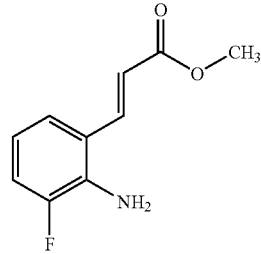

Starting with 42.00 g (221.04 mmol) of 2-bromo-6-fluoroaniline, the general procedure [A] gives 29.66 g (68% of theory) of product.

HPLC (method 1): R$_t$=4.14 min

MS (ESI-pos): m/z=196 (M+H)$^+$

Example 2A

Methyl 2-amino-3-[(1E)-3-methoxy-3-oxo-1-propenyl]benzoate

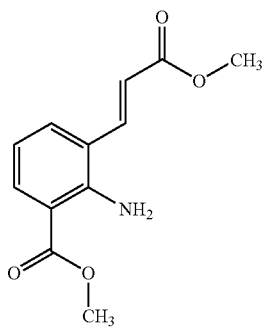

Starting with 2.00 g (8.69 mmol) of methyl 2-amino-3-bromobenzoate, the general procedure [A] gives 1.29 g (60% of theory) of product.

HPLC (method 1): $R_t$=4.42 min
MS (ESI-pos): m/z=236 (M+H)$^+$

Example 3A

Methyl (2E)-3-(2-amino-3,5-difluorophenyl)-2-propenoate

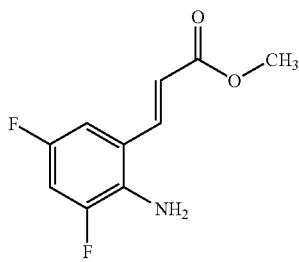

Starting with 3.00 g (14.42 mmol) of 2-bromo-4,6-difluoroaniline, the general procedure [A] gives 1.41 g (45% of theory) of product.

HPLC (method 1): $R_t$=4.23 min
MS (ESI-pos): m/z=214 (M+H)$^+$

Example 4A

Methyl 4-amino-3-[(1E)-3-methoxy-3-oxo-1-propenyl]benzoate

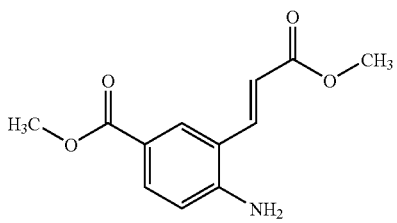

Starting with 25.00 g (90.23 mmol) of methyl 4-amino-3-iodobenzoate, the general procedure [A] gives 24.31 g (92% of theory) of product.

HPLC (method 1): $R_t$=4.71 min
MS (EI-pos): m/z=278 (M+H)$^+$

Example 5A

Methyl (2E)-3-[2-amino-5-cyanophenyl]-2-propenoate

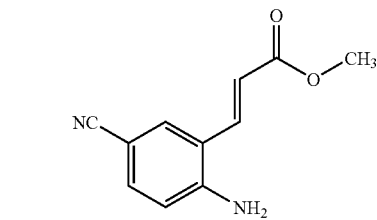

Starting with 1.90 g (9.64 mmol) of 3-bromo-4-aminobenzonitrile, the general procedure [A] gives 1.28 g (50% of theory) of product.

HPLC (method 1): $R_t$=2.85 min
MS (DCI-pos): m/z=220 (M+NH$_4$)$^+$

General Procedure [B]: Synthesis of Substituted 2-nitrocinnamic Acid Derivatives from 2-halo-substituted Benzaldehydes by Wittig-Horner Reaction In a 100 ml one-necked flask, 27.5 mmol of methyl diethylphosphonoacetate, 25.0 mmol of the benzaldehyde and 27.5 mmol of lithium hydroxide are suspended in tetrahydrofuran. After the reaction has ended (the reaction is monitored by TLC), an identical volume of water is added to the mixture. The aqueous phase is extracted three times with ethyl acetate. The combined organic phases are then washed with saturated sodium chloride solution and dried over sodium sulphate, and the solvent is removed. Without further purification, the product is dried under high vacuum at RT. In cases where many impurities are present, the product may be purified by column chromatography on silica gel using cyclohexane/ethyl acetate.

Example 6A

Methyl (2E)-3-(3-methoxy-2-nitrophenyl)-2-propenoate

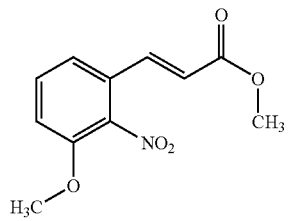

Starting with 2.00 g (11.04 mmol) of 3-methoxy-2-nitrobenzaldehyde, the general procedure [B] gives 2.46 g (92% of theory) of product.

HPLC (method 1): $R_t$=4.37 min

MS (ESI-pos): m/z=238 (M+H)$^+$

Example 7A

Methyl (2E)-3-(5-fluoro-2-nitrophenyl)-2-propenoate

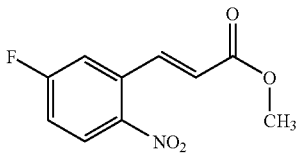

Starting with 20.0 g (118.3 mmol) of 5-fluoro-2-nitrobenzaldehyde, the general procedure [B] gives 7.25 g (27% of theory) of product.

MS (DCI): m/z=243 (M+NH$_4$)$^+$

General Procedure [C]: Preparation of a 2-nitrobenzaldehyde from a Benzyl Halide 10.0 mmol of benzyl halide, 4.1 g of molecular sieve 4 Å and 20.0 mmol of N-methylmorpholine N-oxide are suspended in 45 ml of acetonitrile. Until complete conversion (the reaction is monitored by TLC), the mixture is stirred at RT. After the reaction has ended, the molecular sieve is filtered off, the solvent is evaporated and the residue is taken up again in ethyl acetate. This solution is washed initially with 1N hydrochloric acid and then with saturated sodium chloride solution. The organic phase is separated off and then dried over sodium sulphate, and the solvent is evaporated again. According to an analytical examination, the crude product is sufficiently pure and can directly be reacted further.

Example 8A

2-Fluoro-6-nitrobenzaldehyde

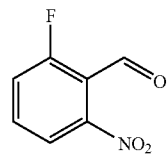

Starting with 2.00 g (8.55 mmol) of 3-fluoro-6-nitrobenzyl bromide, the general procedure [C] gives 1.09 g (75% of theory) of product.

HPLC (method 1): $R_t$=3.58 min

General Procedure [D]: Reduction of the Nitro Group of the 2-nitrocinnamic Acid Derivatives Under argon, 25 mmol of the nitro compound and 125 mmol of tin(II) chloride dihydrate are initially charged in 60 ml of absolute ethanol or methanol in a 250 ml two-necked flask. This suspension is stirred under reflux for 30 minutes, and a clear solution is formed. The solution is then allowed to cool to room temperature and subsequently poured into icewater. Using either solid sodium bicarbonate or a saturated sodium carbonate solution, the pH is adjusted to pH=7-8. 60 ml of ethyl acetate are then added, and the precipitated tin salts are filtered off through kieselguhr (a layer of a thickness of about 1 cm). The organic phase is separated off and the aqueous phase is re-extracted once with ethyl acetate. The organic phases are combined, washed once with saturated sodium chloride solution and dried over sodium sulphate, and the solvent is concentrated to about half of its original volume. Activated carbon corresponding to 1% of the weight of the nitro compound is then added, and the mixture is heated under reflux for 30 minutes (the colour of the solution changes). The activated carbon is filtered off and the solvent is evaporated.

The residue that remains is an oil which, on drying at RT under high vacuum, forms crystals. Without further purification, it is used directly for the next step.

Example 9A

Methyl 3-[2-amino-6-fluorophenyl]propenoate

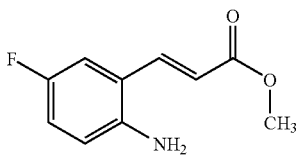

Starting with 7.25 g (32.2 mmol) of the nitro compound from Example 7A, the general procedure [D] gives 5.0 g (58% of theory) of product.

HPLC (method 1): $R_t$=3.33 min

General Procedure [E]: Synthesis of the N-arylpiperidine-4-carboxylic Esters by Buchwald-Hartwig Chemistry The reaction is carried out under argon in a flask which was thoroughly dried by heating. 24.7 mmol of the bromobenzene, 74 mmol of piperidine-4-carboxylic ester and 34.5 mmol of sodium tert-butoxide are initially charged in 100 ml of absolute toluene, 0.25 mmol of tris(dibenzylideneacetone) dipalladium and 0.74 mmol of BINAP are added, and the reaction mixture is heated to 120° C. and heated under reflux for 16 hours. The reaction is terminated and the reaction mixture is extracted successively once with water and twice with 1N hydrochloric acid. The acidic aqueous phase is then adjusted to pH 8 using 1N aqueous sodium hydroxide solution and extracted three times with dichloromethane. The combined organic phases are dried over sodium sulphate and filtered, and the solvent is removed under reduced pressure. The crude product obtained in this manner can be reacted further directly, without further purification.

Example 10A

Methyl N-(4-fluoro-3-methylphenyl)piperidine-4-carboxylate

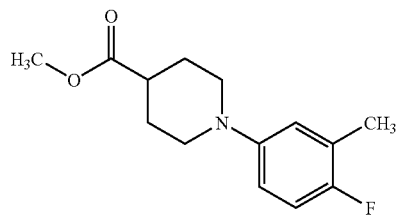

starting with 10.6 g (74.0 mmol) of methyl piperidine-4-carboxylate and 4.67 g (24.7 mmol) of 5-bromo-2-fluorotoluene, the general procedure [E] gives 2.74 g (40% of theory) of product.

HPLC (method 1): $R_t$=3.48 min

Examples 11A to 17A from the table below can be prepared in accordance with the general procedure [E].

| Ex. No. | Structure | Starting material A Amount of starting material A Starting material B Amount of starting material B | Yield | HPLC $R_t$ [min] (method) |
|---|---|---|---|---|
| 11A | 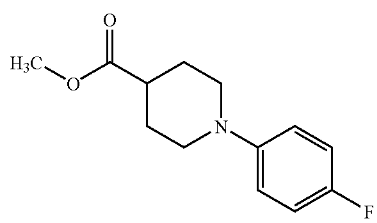 | methyl piperidine-4-carboxylate 10.6 g (74.0 mmol) 4-fluoro-bromobenzene 4.32 g (24.7 mmol) | 5.77 g (62% of theory) | 3.25 (1) |
| 12A | 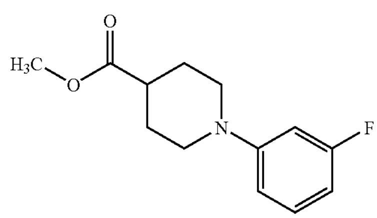 | methyl piperidine-4-carboxylate 10.6 g (74.0 mmol) 3-fluoro-bromobenzene 4.32 g (24.7 mmol) | 3.19 g (54% of theory) | 3.41 (1) |
| 13A | 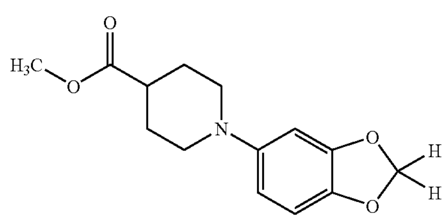 | methyl piperidine-4-carboxylate 10.6 g (74.0 mmol) 3,4-dioxolan-bromobenzene 4.96 g (24.7 mmol) | 3.75 (44% of theory) | 3.27 (1) |
| 14A | 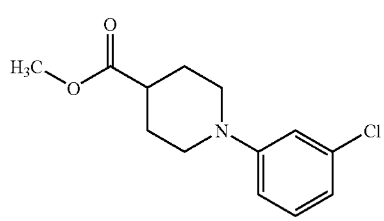 | methyl piperidine-4-carboxylate 22.4 g (156.7 mmol) 3-chlorobromobenzene 10.00 g (52.3 mmol) | 6.78 g (51% of theory) | 3.74 (1) |

-continued

| Ex. No. | Structure | Starting material A<br>Amount of starting material A<br>Starting material B<br>Amount of starting material B | Yield | HPLC $R_t$ [min] (method) |
|---|---|---|---|---|
| 15A | methyl 1-(3-methylphenyl)piperidine-4-carboxylate | methyl piperidine-4-carboxylate<br>5.02 g (35.1 mmol)<br>3-methyl-bromobenzene<br>2.00 g (11.7 mmol) | 0.59 g (9% of theory) | 3.46 (1) |
| 16A | ethyl 1-(3-methoxyphenyl)piperidine-4-carboxylate | ethyl piperidine-4-carboxylate<br>5.00 g (31.8 mmol)<br>3-methoxy-bromobenzene<br>1.98 g (10.6 mmol) | 1.66 g (59% of theory) | 3.60 (1) |
| 17A | ethyl 1-(4-fluoro-3-methoxyphenyl)piperidine-4-carboxylate | ethyl piperidine-4-carboxylate<br>3.68 g (23.41 mmol)<br>4-bromo-1-fluoro-2-methoxybenzene<br>1.60 g (7.80 mmol) | 1.32 g (60% of theory) | 3.60 (1) |

General Procedure [F]: Hydrolysis of the N-arylpiperidine-4-carboxylic Esters 1.0 equivalent of the N-arylpiperidine-4-carboxylic ester is dissolved in dioxane, and 2.0 equivalents of 1N aqueous sodium hydroxide solution are added. The mixture is stirred at 80° C. for 16 hours, and after the reaction has ended (the reaction is monitored by analytical HPLC) the mixture is concentrated. The residue is then taken up in water and adjusted to pH=5 using 1N hydrochloric acid. The resulting precipitate is filtered off, washed with a little water and cyclohexane and dried at room temperature under high vacuum. If the purity of the product is not high enough, the product is purified by preparative HPLC on an RP phase.

Example 18A

N-(4-Fluoro4-methylphenyl)piperidine-4-carboxylic acid

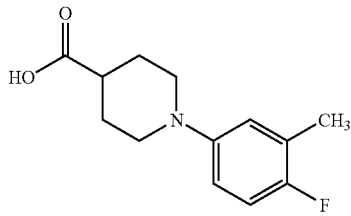

Starting with 2.57 g (10.7 mmol) of the ester from Example 10A, the general procedure [F] gives 1.48 g (58% of theory) of product.

HPLC (method 1): $R_t$=3.35 min

Examples 19A to 25A from the table below can be prepared in accordance with the general procedure [F].

| Ex. No. | Structure | Starting material Amount of starting material | Yield | HPLC $R_t$ [min] (method) |
|---|---|---|---|---|
| 19A | 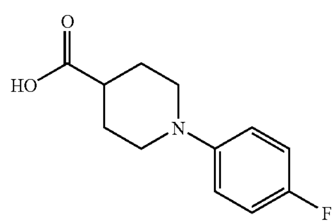 | Example 11A 5.7 g (24.0 mmol) | 2.06 g (38% of theory) | 2.77 (1) |
| 20A | 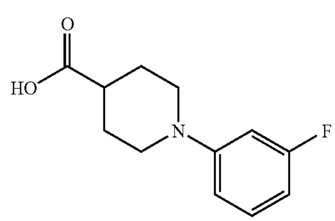 | Example 12A 3.19 g (13.4 mmol) | 2.5 g (83% of theory) | 3.05 (1) |
| 21A | 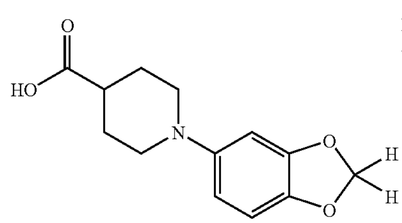 | Example 13A 3.75 g (14.2 mmol) | 2.85 g (80% of theory) | 2.98 (1) |
| 22A | 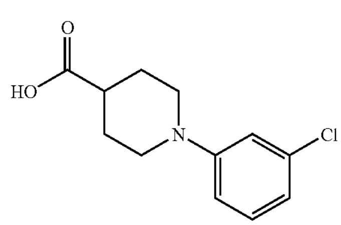 | Example 14A 6.73 g (26.5 mmol) | 5.55 g (76% of theory) | 3.36 (1) |

| Ex. No. | Structure | Starting material Amount of starting material | Yield | HPLC $R_t$ [min] (method) |
|---|---|---|---|---|
| 23A | (piperidine-4-carboxylic acid, N-(3-methylphenyl)) | Example 15A 0.59 g (1.09 mmol) | 0.13 g (48% of theory) | 1.13 (3) |
| 24A | (piperidine-4-carboxylic acid, N-(3-methoxyphenyl)) | Example 16A 1.57 g (5.96 mmol) | 1.12 g (80% of theory) | 3.10 (1) |
| 25A | (piperidine-4-carboxylic acid, N-(4-fluoro-3-methoxyphenyl)) | Example 17A 5.72 g (20.33 mmol) | 4.98 g (97% of theory) | 3.20 (1) |

General Procedure [G]: Acylation of the 2-aminocinnamic Esters with N-arylpiperidine-4-carboxylic Acid 6.3 mmol of the N-arylpiperidine-4-carboxylic acid are initially charged in 75 ml of dichloromethane, a drop of DMF is added and 18.7 mmol of oxalyl chloride are, with ice-cooling, added to the mixture. After the addition has ended, the reaction mixture is heated under reflux for 1 h and cooled, and the solvent is removed under reduced pressure. The residue is taken up in 60 ml of dichloromethane and, with ice-cooling, added dropwise to a solution of 5.7 mmol of 2-aminocinnamic ester and 18.7 mmol of pyridine or triethylamine in 20 ml of dichloromethane. After the addition has ended, the mixture is heated under reflux for 2 h. The solvent is then removed under reduced pressure and the residue is taken up in dichloromethane. The organic phase is extracted twice with water and once with saturated sodium bicarbonate solution and dried over sodium sulphate. The sodium sulphate is filtered off and the solvent is removed under reduced pressure. The residue is triturated with diethyl ether and a few drops of ethyl acetate, and the precipitate is filtered off and washed with diethyl ether. The product is dried under reduced pressure. If the product is not pure enough for further reactions, it is purified chromatographically.

Example 26A

Methyl (2E)-3-fluoro-2-({[1-(4-fluoro-3-methyl)piperidin-4-yl]carbonyl}amino)-phenyl acrylate

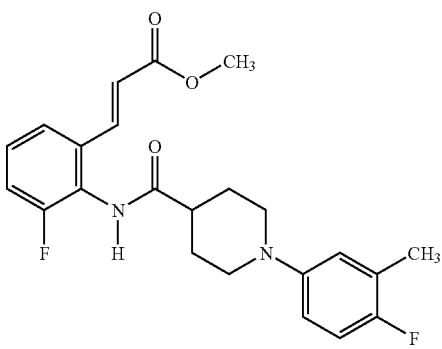

Starting with 1.48 g (6.23 mmol) of the carboxylic acid from Example 18A and 1.11 g (5.67 mmol) of aniline from Example 1A, the general procedure [G] gives 7.77 g (79% of theory) of product.

HPLC (method 1): $R_t$=4.05 min

Examples 27A to 33A from the table below can be prepared in accordance with the general procedure [G].

| Ex. No. | Structure | Aniline Amount of aniline Acid Amount of acid | Yield | HPLC $R_t$ [min] (method) |
|---|---|---|---|---|
| 27A | 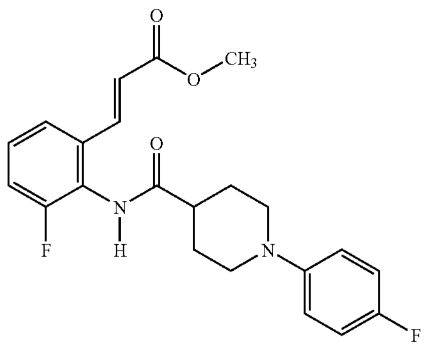 | Example 1A 4.81 g (24.67 mmol) Example 19A 5.8 g (25.98 mmol) | 4.70 g (48% of theory) | 3.80 (6) |
| 28A | 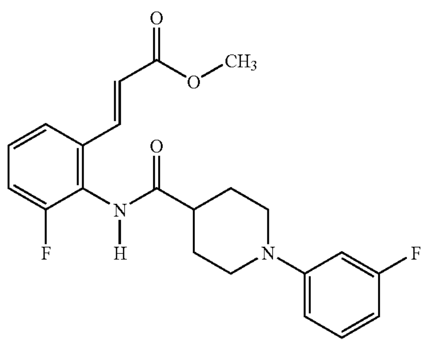 | Example 1A 1.99 g (10.2 mmol) Example 20A 2.5 g (11.2 mmol) | 3.75 g (92% of theory) | 3.97 (1) |
| 29A | 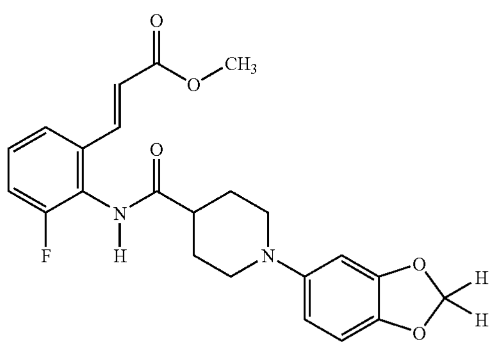 | Example 1A 2.03 g (10.4 mmol) Example 21A 2.85 g (11.4 mmol) | 1.79 g (39% of theory) | 3.89 (1) |
| 30A | 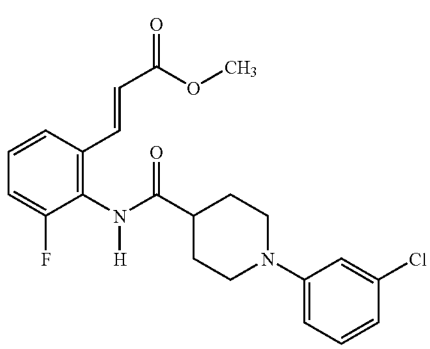 | Example 1A 1.9 g (9.9 mmol) Example 22A 3.0 g (10.9 mmol) | 2.78 g (68% of theory) | 4.20 (1) |

-continued

| Ex. No. | Structure | Aniline Amount of aniline Acid Amount of acid | Yield | HPLC $R_t$ [min] (method) |
|---|---|---|---|---|
| 31A | (structure) | Example 1A 0.22 g (1.11 mmol) Example 23A 0.29 g (1.20 mmol) | 0.21 g (46% of theory) | 3.99 (6) |
| 32A | (structure) | Example 1A 0.87 g (4.45 mmol) Example 24A 1.1 g (4.68 mmol) | 0.47 g (26% of theory) | 4.00 (1) |
| 33A | (structure) | Example 1A 0.73 g (3.76 mmol) Example 25A 2.40 g (9.48 mmol) | 0.25 g (15% of theory) | 4.00 (1) |

General Procedure [H]: Cyclization of the 2-aminoacylcinnamic Esters with Anilines At room temperature, 1.2 mmol of the 2-aminoacylcinnamic ester and 7.24 mmol of phosphorus oxychloride are initially charged in 10 ml of toluene. With vigorous stirring, the mixture is heated under reflux (bath temperature 120-125° C.) for 16 h. The solvent is then distilled off under reduced pressure and codistilled once with toluene. The mixture is once again taken up in 10 ml of toluene, and 3.6 mmol of the aniline are added. The mixture is heated at reflux for 24 h. The solvent is then removed under reduced pressure and the residue is taken up in dichloromethane and extracted twice with 1N hydrochloric acid. The organic phase is dried over sodium sulphate and filtered, and the solvent is removed under reduced pressure. The product is purified chromatographically on silica gel or by preparative HPLC (method 4).

Example 34A

Methyl {8-fluoro-2-[1-(4-fluoro-3-methylphenyl)piperidin-4-yl]-3-[2-methoxy-5-(trifluoromethyl)phenyl]-3,4-dihydroquinazolin-4-yl}acetate

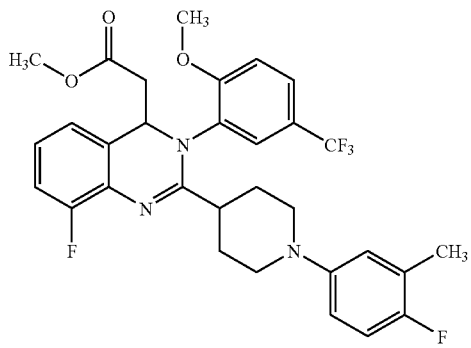

Starting with 0.6 g (1.45 mmol) of the 2-acylaminocinnamic ester from Example 26A, the general procedure [H] and purification by preparative HPLC (method 4) and chromatography on silica gel using cyclohexane/ethyl acetate 8:2 (v/v) gives 355 mg (39% of theory) of product.
HPLC (method 1): $R_t$=4.52 min
MS: m/z=588 (M+H)$^+$ Example 35A Methyl {8-fluoro-2-[1-(4-fluoro-3-methylphenyl)piperidin-4-yl]-3-[2-methoxy-5-(trifluoromethyl)phenyl]-3,4-dihydroquinazolin-4-yl}acetate

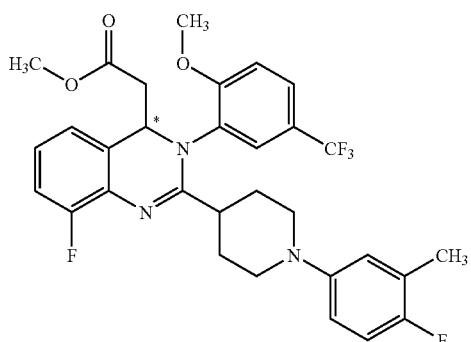

Starting with 355 mg (0.6 mmol) of racemate from Example 34A, chromatographic separation of the enantiomers (method 2) gives 148 mg (42% of theory) of the compound as enantiomer B.

Example 36A

Methyl {8-fluoro-2-[1-(4-fluorophenyl)piperidin-4-yl]-3-[2-methoxy-5-(trifluoromethyl)phenyl]-3,4-dihydroquinazolin-4-yl}acetate

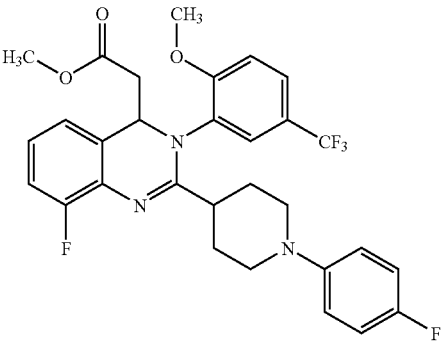

Starting with 300 mg (0.75 mmol) of the 2-acylaminocinnamic ester from Example 27A, the general procedure [H] gives 298 mg (69% of theory) of product.
HPLC (method 1): $R_t$=4.30 min
MS (ESI pos): m/z=574 (M+H)$^+$ Example 37A Methyl {8-fluoro-3-(2-methoxy-5-(trifluoromethyl)phenyl)-2-[1-(3-methylphenyl)-piperidin-4-yl]-3,4-dihydroquinazolin-4-yl}acetate

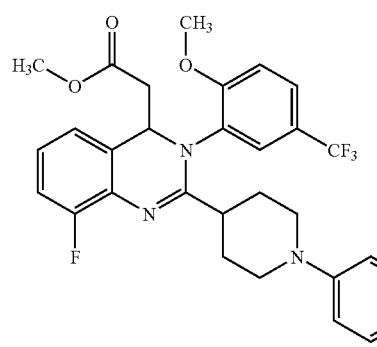

Starting with 0.057 g (0.14 mmol) of the 2-acylaminocinnamic ester from Example 31A, the general procedure [H] and purification by preparative HPLC (method 4) gives 32 mg (35% of theory) of product.
HPLC (method 1): $R_t$=4.44 min
MS: m/z=570 (M+H)$^+$ Working Examples
General Procedure [I]: Hydrolysis of the Quinazolylacetic Esters 1.0 equivalent of the quinazolylacetic ester is dissolved in dioxane, and 5.0 equivalents of 1N aqueous sodium hydroxide solution are added. The mixture is stirred at 80° C. for 16 hours and, after the reaction has ended (monitoring of reaction by means of analytical HPLC), the mixture is concentrated. The residue is then taken up in water and adjusted to pH=5 using 1N hydrochloric acid. The resulting precipitate is filtered off, washed with a little water and diethyl ether and dried under high vacuum or in a drying cabinet. If the purity of the product is not high enough, the product is purified by preparative HPLC on an RP phase (method 4) or by chromatography on silica gel.

Example 1

{8-Fluoro-2-[1-(4-fluoro-3-methylphenyl)piperidin-4-yl]-3-[2-methoxy-5-(trifluoromethyl)phenyl]-3,4-dihydroquinazolin-4-yl}acetic acid hydrochloride

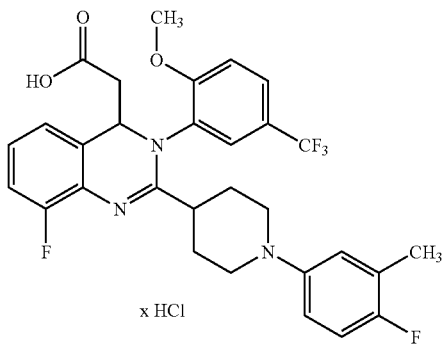

Starting with 50 mg (0.085 mmol) of the methyl ester from Example 34A, the general procedure [I] and concentration of the product from a mixture of methanol/1N hydrochloric acid gives 13 mg (24% of theory) of product.

HPLC (method 1): $R_f$=4.27 min

MS (ESI pos): m/z=574 (M+H)$^+$ $^1$H-NMR (400 MHz, CD$_3$CN): δ [ppm]=8.05-7.82 (m, 2H), 7.65-7.38 (m, 3H), 7.30 (d, 1H), 7.29-7.12 (m, 2H), 7.00 (d, 1H), 5.40 and 5.25 (2s, 1H), 4.00-3.75 (2s, 3H), 3.75-2.70 (m, 9H), 2.70-2.00 (m, 2H). (The $^1$H-NMR indicates the presence of rotational isomers.)

Example 2

{8-Fluoro-2-[1-(4-fluoro-3-methylphenyl)piperidin-4-yl]-3-[2-methoxy-5-(trifluoromethyl)phenyl]-3,4-dihydroquinazolin-4-yl}acetic acid hydrochloride

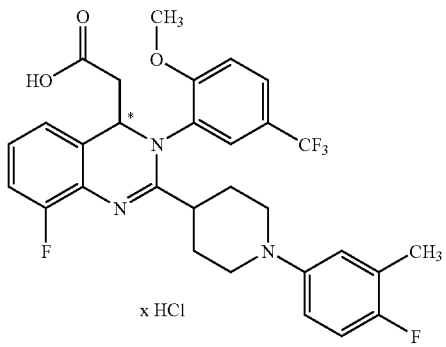

Starting with 148 mg (0.25 mmol) of the methyl ester from Example 35A, the general procedure [I] and concentration of the product from a mixture of methanol/1N hydrochloric acid gives 62 mg (40% of theory) of product.

HPLC (method 1): $R_f$=4.27 min

MS (ESI pos): m/z=574 (M-HCl+H)$^+$ $^1$H-NMR (400 MHz, CD$_3$CN): δ [ppm]=8.00-7.55 (m, 2H), 7.55-6.75 (m, 7H), 5.25 and 5.05 (2s, 1H), 3.95 and 3.75 (2s, 3H), 3.70-3.48 (d, 2H), 3.05-2.00 (m, 7H). (The $^1$H-NMR indicates the presence of rotational isomers.)

Example 3

{8-Fluoro-3-[2-methoxy-5-(trifluoromethyl)phenyl]-2-[1-(3-methylphenyl)piperidin-4-yl]-3,4dihydroquinazolin-4-yl}acetic acid

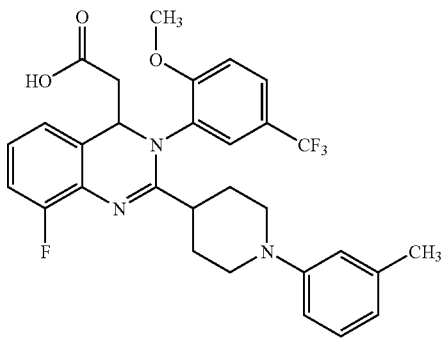

Starting with 41 mg (0.07 mmol) of the methyl ester from Example 37A, the general procedure [I] and concentration of the product from a mixture of methanol/1N hydrochloric acid and subsequent purification by chromatography (method 4) gives 13 mg (31% of theory) of product.

HPLC (method 7): $R_f$=2.64 min

MS (ESI pos): m/z=556 (M+H)$^+$ $^1$H-NMR (400 MHz, D$_2$O): δ [ppm]=7.94-7.80 (m, 3H), 7.42-6.93 (m, 7H), 5.45-5.27 (m, 2H), 3.90 (s, 3H), 3.85-3.54 (m, 2H), 3.27-3.02 (m, 2H), 2.96-2.68 (m, 3H), 2.38-1.93 (m, 6H). (The $^1$H-NMR indicates the presence of rotational isomers.)

Example 4

{8-Fluoro-2-[1-(4-fluorophenyl)piperidin-4-yl]-3-[2-methoxy-5-(trifluoromethyl)-phenyl]-3,4-dihydroquinazolin-4-yl}acetic acid

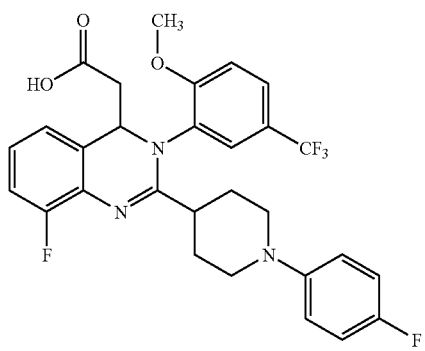

Starting with 50.00 mg (0.09 mmol) of the methyl ester from Example 36A, the general procedure [I] gives 30 mg (62% of theory) of product.

HPLC (method 1): $R_t$=4.20 min

MS (DCI/NH$_3$): m/z=560 (M+H)$^+$ $^1$H-NMR (400 MHz, CDCl$_3$): δ [ppm]=7.85-7.50 (m, 2H), 7.35-6.60 (m, 8H), 4.95 (m, 1H), 3.95 and 3.75 (2s, 3H), 3.20-1.50 (m, 10H). (The $^1$H-NMR indicates the presence of rotational isomers.)

Examples 5 to 24 from the table below can be prepared according to the general procedures [H] and [I]. If required, hydrochlorides can be obtained after the reaction by concentrating the product from a mixture of methanol/1N hydrochloric acid.

| Ex. No. | Structure | Molecular weight | Isomer | HPLC $R_t$ [min] (method) | MS m/z |
|---|---|---|---|---|---|
| 5 | 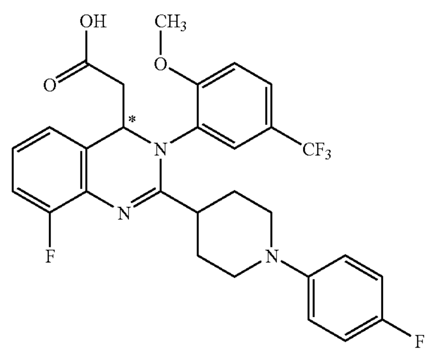 | 559.5 | enantiomer B | 4.20 (1) | 560 [M + H]$^+$ |
| 6 | 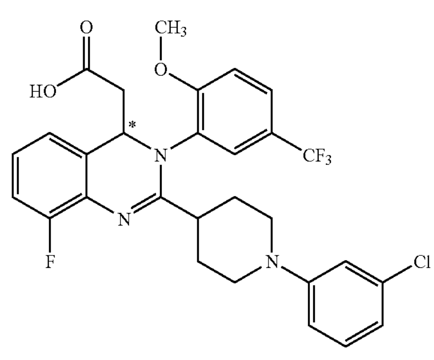 | 576 | enantiomer B | 4.65 (1) | 576 [M + H]$^+$ |

-continued

| Ex. No. | Structure | Molecular weight | Isomer | HPLC $R_t$ [min] (method) | MS m/z |
|---|---|---|---|---|---|
| 7 | 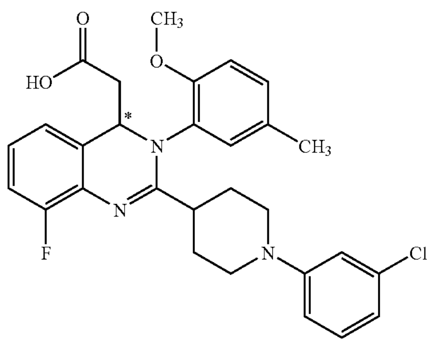 | 522 | enantiomer B | 4.78 (1) | 522 [M + H]⁺ |
| 8 | 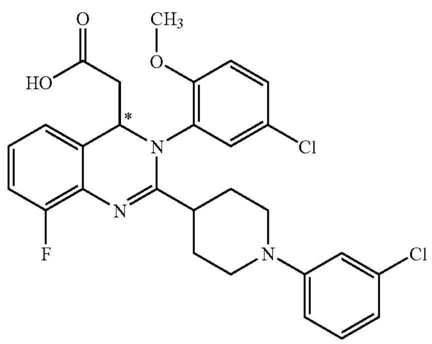 | 542.4 | enantiomer B | 4.64 (1) | 542 [M + H]⁺ |
| 9 | 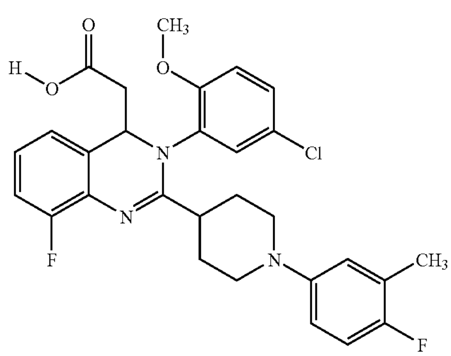 | 540 | racemate | 4.13 (1) | 540 [M + H]⁺ |
| 10 | 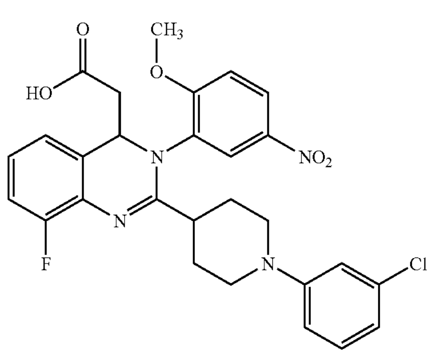 | 553 | racemate | 4.50 (1) | 553 [M + H]⁺ |

-continued

| Ex. No. | Structure | Molecular weight | Isomer | HPLC R$_t$ [min] (method) | MS m/z |
|---|---|---|---|---|---|
| 11 | 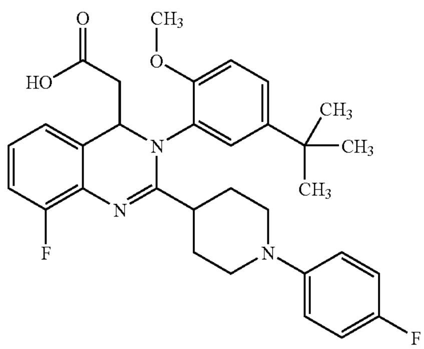 | 547.6 | racemate | 4.40 (6) | 548 [M + H]$^+$ |
| 12 | 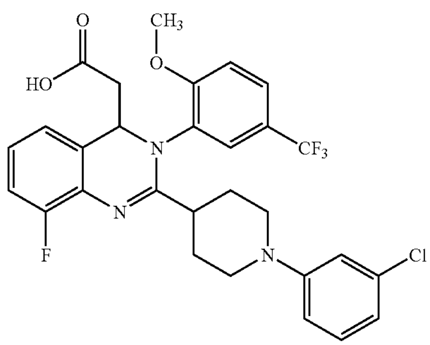 | 576 | racemate | 4.77 (1) | 576 [M + H]$^+$ |
| 13 | x HCl | 588.5 | racemate | 3.96 (6) | 552 [M − HCl + H]$^+$ |
| 14 | x HCl | 596 | racemate | 4.53 (1) | 560 [M − HCl + H]$^+$ |

-continued

| Ex. No. | Structure | Molecular weight | Isomer | HPLC R$_t$ [min] (method) | MS m/z |
|---|---|---|---|---|---|
| 15 | 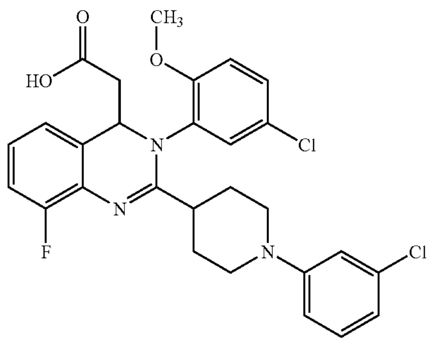 | 542.4 | racemate | 4.76 (1) | 542 [M + H]$^+$ |
| 16 | 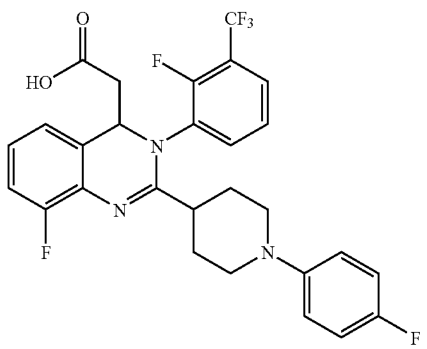 | 547.5 | racemate | 4.10 (6) | 548 [M + H]$^+$ |
| 17 | 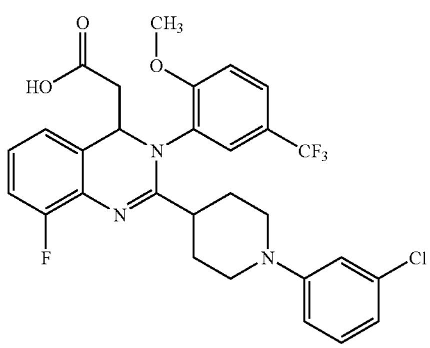 | 522 | racemate | 4.70 (1) | 522 [M + H]$^+$ |
| 18 | x HCl | 556.1 | racemate | 4.10 (1) | 520 [M − HCl + H]$^+$ |

-continued

| Ex. No. | Structure | Molecular weight | Isomer | HPLC R_t [min] (method) | MS m/z |
|---|---|---|---|---|---|
| 19 | 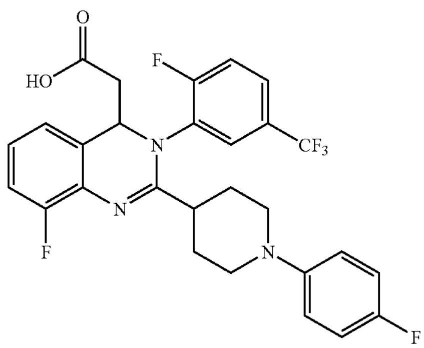 | 547.5 | racemate | 4.10 (1) | 548 [M + H]+ |
| 20 | 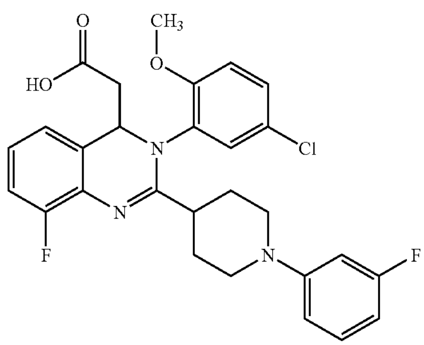 | 562.4 | racemate | 4.39 (1) | 526 [M − HCl + H]+ |
| 21 | 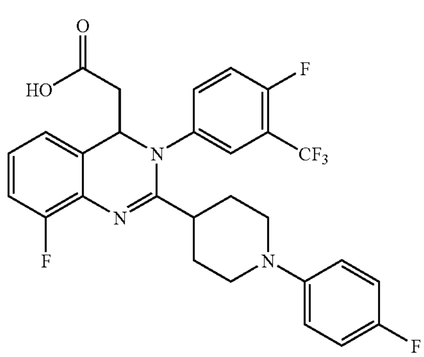 | 547.5 | racemate | 4.20 (1) | 548 [M + H]+ |
| 22 | 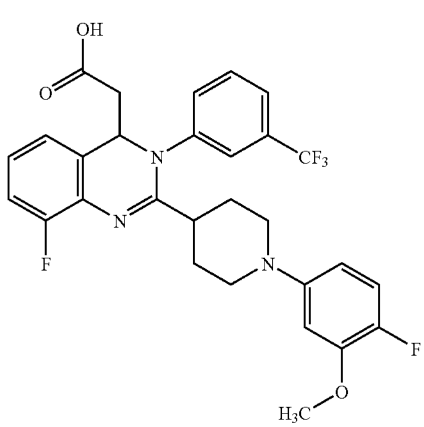 | 559.5 | racemate | 4.20 (1) | 560 [M + H]+ |

-continued

| Ex. No. | Structure | Molecular weight | Isomer | HPLC R$_t$ [min] (method) | MS m/z |
|---|---|---|---|---|---|
| 23 | 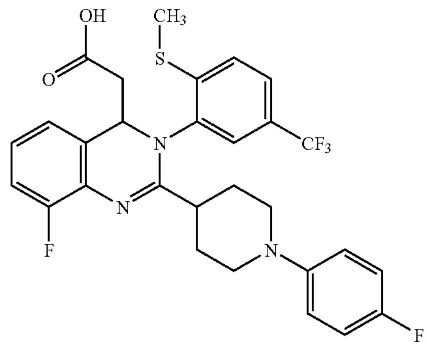 | 575.6 | racemate | 4.20 (6) | 576 [M + H]$^+$ |
| 24 | 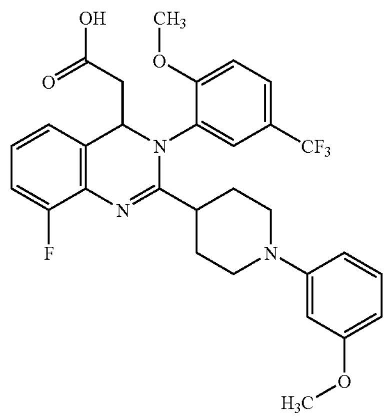 | 571.6 | racemate | 4.20 (1) | 572 [M + H]$^+$ |

B. ASSESSMENT OF THE PHYSIOLOGICAL ACTIVITY

The in vitro effect of the compounds of the invention can be shown in the following assays:
Anti-HCMV (Anti-Human Cytomegalovirus) Cytopathogenicity Tests The test compounds are employed as 50 millimolar (mM) solutions in dimethyl sulphoxide (DMSO). Ganciclovir, Foscarnet and Cidofovir are used as reference compounds. After addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. Then 150 µl portions of a suspension of 1×10$^4$ cells (human prepuce fibroblasts [NHDF]) are pipetted into each of the wells (row 1=cell control) and, in rows 2-12, a mixture of HCMV-infected and uninfected NHDF cells (M.O.I.=0.001-0.002), i.e. 1-2 infected cells-per 1000 uninfected cells. Row 12 (without substance) serves as virus control. The final test concentrations are 250-0.0005 µM. The plates are incubated at 37° C./5% CO$_2$ for 6 days, i.e. until all the cells are infected in the virus controls (100% cytopathogenic effect [CPE]). The wells are then fixed and stained by adding a mixture of formalin and Giemsa's dye (30 minutes), washed with double-distilled water and dried in a drying cabinet at 50° C. The plates are then assessed visually using an overhead microscope (Plaque Multiplier from Technomara).

The following data can be acquired from the test plates:
CC$_{50}$ (NHDF)=substance concentration in µM at which no visible cytostatic effects on the cells are evident by comparison with the untreated cell control;
EC$_{50}$ (HCMV)=substance concentration in µM which inhibits the CPE (cytopathic effect) by 50% compared with the untreated virus control;
SI (selectivity index)=CC$_{50}$ (NHDF)/EC$_{50}$ (HCMV).
Representative in vitro data for the effects of the compounds of the invention are shown in Table A:

TABLE A

| Example No. | NHDF CC$_{50}$ [µM] | HCMV EC$_{50}$ [µM] | SI HCMV |
|---|---|---|---|
| 1 | 24 | 0.03 | 800 |
| 2 | 31 | 0.04 | 775 |
| 3 | 31 | 0.1 | 310 |
| 4 | 36 | 0.15 | 237 |

The suitability of the compounds of the invention for the treatment of HCMV infections can be shown in the following animal model:
HCMV Xenograft Gelfoam® Model
Animals: 3-4-week old female immunodeficient mice (16-18 g), Fox Chase SCID or Fox Chase SCID-NOD or SCID beige, are purchased from commercial breeders (Bomholtgaard, Jackson). The animals are housed under sterile conditions (including bedding and feed) in isolators.

Virus growing: Human cytomegalovirus (HCMV), Davis strain, is grown in vitro on human embryonic prepuce fibroblasts (NHDF cells). After the NHDF cells have been infected with a multiplicity of infection (M.O.I.) of 0.01, the virus-infected cells are harvested 5-7 days later and stored in the presence of minimal essential medium (MEM), 10% foetal calf serum (FCS) with 10% DMSO at −40° C. After serial ten-fold dilutions of the virus-infected cells, the titre is determined on 24-well plates of confluent NHDF cells after vital staining with Neutral Red, or fixation and staining with a formalin/Giemsa mixture (as described above).

Preparation of the sponges, transplantation, treatment and evaluation: Collagen sponges 1×1×1 cm in size (Gelfoam®; from Peasel & Lorey, order No. 407534; K. T. Chong et al., Abstracts of 39th Interscience Conference on Antimicrobial Agents and Chemotherapy, 1999, p. 439; P. M. Kraemer et al., Cancer Research 1983, (43): 4822-4827) are initially wetted with phosphate-buffered saline (PBS), the trapped air bubbles are removed by degassing, and then stored in MEM+10% FCS. 1×106 virus-infected NHDF cells (infection with HCMV Davis M.O.I.=0.01) are detached 3 hours after infection and added in a drop of 20 µl of MEM, 10% of FCS, to a moist sponge. 12-13 hours later, the infected sponges are optionally applied to 25 µl of PBS/0.1% BSA/1 mM DTT with 5 ng/µl basic fibroblast growth factor (bFGF) and incubated for 1 hour. For the transplantation, the immunodeficient mice are anaesthetized with Avertin or a mixture of xylazine/azepromazine and ketamine, the fur on the back is removed using a shaver, the epidermis is opened 1-2 cm, unstressed and the moist sponges are transplanted under the dorsal skin. The surgical wound is closed with tissue glue. 24 hours after the transplantation, the mice are, over a period of 8 days, treated with substance perorally three times a day (7.00 h and 14.00 h and 19.00 h), two times a day (8.00 h and 17.00 h) or once a day (14.00 h). The dose is 3 or 10 or 30 or 100 mg/kg of body weight, the volume administered is 10 ml/kg of body weight. The substances are formulated in the form of a 0.5% strength. Tylose suspension, optionally with 2% DMSO. 9 days after transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% foetal calf serum, 10% DMSO at −140° C. Evaluation takes place after serial ten-fold dilutions of the virus-infected cells by determining the titre on 24-well plates of confluent NHDF cells after vital staining with Neutral Red or after fixation and staining with a formalin/Giemsa mixture (as described above). The number of infectious virus particles after the substance treatment compared with the placebo-treated control group is determined.

C. EXEMPLARY EMBODIMENTS OF PHARMACEUTICAL COMPOSITIONS

The compounds of the invention can be converted into pharmaceutical preparations in the following ways:

Tablet:

Composition: 100 mg of the compound of Example 1, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Production: The mixture of active ingredient, lactose and starch is granulated with a 5% strength solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:

Composition: 1000 mg of the compound of Example 1, 1000 mg of ethanol (96%), 400 mg of Rhodigel (xanthan gum from FMC, Pennsylvania, USA) and 99 g of water.

10 ml of oral suspension are equivalent to a single dose of 100 mg of the compound of the invention.

Production: The Rhodigel is suspended in ethanol, and the active ingredient is added to the suspension. The water is added while stirring. The mixture is stirred for about 6 h until the swelling of the Rhodigel is complete.

The invention claimed is:

1. A compound of formula (I)

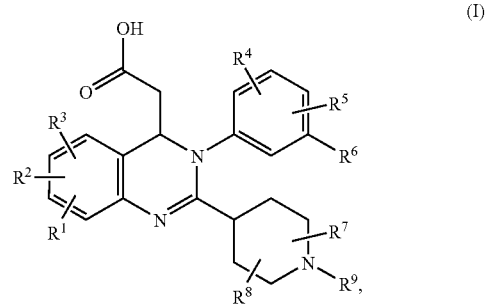

in which $R^1$, $R^2$ and $R^3$ independently of one another represent hydrogen, alkyl, alkoxy, carboxyl, alkylcarbonyl, alkoxycarbonyl, aminocarbonyl, trifluoromethyl, halogen, cyano, hydroxyl or nitro, $R^4$ and $R^5$ independently of one another represent hydrogen, alkyl, alkoxy, alkylthio, cyano, halogen, nitro, trifluoromethyl or trifluoromethoxy, $R^6$ represents alkyl, cyano, halogen, nitro or trifluoromethyl, $R^7$ and $R^8$ independently of one another represent hydrogen, halogen, alkyl or alkoxy and $R^9$ represents aryl or 1,3-benzodioxol-5-yl, where aryl and 1,3-benzodioxol-5-yl may be substituted by 1 to 3 substituents, where the substituents independently of one another are selected from the group consisting of alkoxy, alkylthio, carboxyl, alkylcarbonyl, alkoxycarbonyl, aminocarbonyl, trifluoromethyl, halogen, carbamoyl, cyano, hydroxyl, amino, alkylamino, nitro and optionally hydroxyl-substituted alkyl, or a salt thereof.

2. The compound according to claim 1, whereby $R^1$, $R^2$ and $R^3$ independently of one another represent hydrogen, methyl, fluorine, chlorine, cyano, hydroxyl or aminocarbonyl, $R^4$ and $R^5$ independently of one another represent hydrogen, fluorine, $C_1$-$C_4$-alkyl or $C_1$-$C_4$-alkoxy, $R^6$ represents chlorine, nitro, trifluoromethyl, methyl, isopropyl or tert-butyl, $R^7$ and $R^8$ independently of one another represent hydrogen or $C_1$-$C_3$-alkyl and $R^9$ represents phenyl or 1,3-benzodioxol-5-yl, where phenyl may be substituted by 1 to 3 substituents, where the substituents independently of one another are selected from the group consisting of $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino and nitro.

3. The compound according to claim 1, whereby
$R^1$ and $R^2$ are hydrogen,
$R^3$ is fluorine,
$R^4$ and $R^5$ independently of one another are hydrogen, fluorine or methoxy,
$R^6$ is trifluoromethyl,
$R^7$ and $R^8$ are hydrogen and
$R^9$ is phenyl, where phenyl may be substituted by 1 or 2 substituents, where the substituents independently of one another are selected from the group consisting of methyl, methoxy, ethoxy, fluorine and chlorine.

4. A method for preparing a compound of formula (I) according to claim 1, comprising the step of reacting a compound of formula (II)

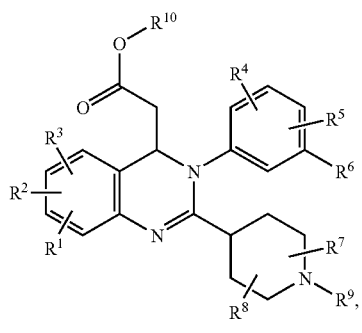

(II)

in which
$R^1, R^2, R^3, R^4, R^5, R^6, R^7, R^8$ and $R^9$ are as defined in claim 1, and
$R^{10}$ represents alkyl,
with a base.

5. A method for preparing a medicament comprising mixing a therapeutically effective amount of a compound according to claim 1 with a pharmaceutically suitable excipient.

6. A method for preparing a medicament for the treatment of viral infections in humans, or the prophylaxis, or treatment and prophylaxis of viral infections in immuno-compromised humans, comprising mixing a therapeutically effective amount of a compound according to claim 1 with a pharmaceutically suitable excipient, wherein the viral infection is an infection with the human cytomegalovirus (HCMV).

7. A medicament comprising a therapeutically effective amount of a compound as defined in claim 1 in combination with a further active compound.

8. A medicament comprising a therapeutically effective amount of a compound as defined in claim 1 in combination with an inert nontoxic, pharmaceutically acceptable auxiliary.

9. A method for treating viral infections in humans by administering an antivirally effective amount of a compound according to claim 1, wherein the viral infection is an infection with the human cytomegalovirus (HCMV) or another representative of the group of herpes viridae.

10. A method for the prophylaxis of viral infections in an immuno-compromised human by administering an antivirally effective amount of a compound according to claim 1 to the immuno-compromised human, wherein the viral infection is an infection with the human cytomegalovirus (HCMV).

\* \* \* \* \*